United States Patent
Fort et al.

(10) Patent No.: US 8,831,256 B2
(45) Date of Patent: Sep. 9, 2014

(54) CONTROLLING A LINK FOR DIFFERENT LOAD CONDITIONS

(75) Inventors: Andrew Fort, Leuven (BE); Adam Schindhelm, Surry Hills (AU); Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 101 days.

(21) Appl. No.: 13/315,691

(22) Filed: Dec. 9, 2011

(65) Prior Publication Data

US 2013/0148828 A1 Jun. 13, 2013

(51) Int. Cl.
*H04R 25/00* (2006.01)

(52) U.S. Cl.
USPC ............. 381/315; 381/314; 381/323; 607/57; 307/104

(58) Field of Classification Search
USPC ................. 381/331, 314–315, 323; 607/57; 307/104
See application file for complete search history.

(56) References Cited

U.S. PATENT DOCUMENTS

| | | | | |
|---|---|---|---|---|
| 5,217,011 A | * | 6/1993 | Bisch | 607/51 |
| 5,741,314 A | * | 4/1998 | Daly et al. | 607/60 |
| 5,876,425 A | * | 3/1999 | Gord et al. | 607/56 |
| 6,073,050 A | * | 6/2000 | Griffith | 607/57 |
| 6,212,431 B1 | | 4/2001 | Hahn et al. | |
| 6,275,737 B1 | * | 8/2001 | Mann | 607/61 |
| 6,745,077 B1 | * | 6/2004 | Griffith et al. | 607/61 |
| 7,171,273 B2 | * | 1/2007 | Shaquer | 607/57 |
| 7,657,045 B2 | * | 2/2010 | Hochmair et al. | 381/312 |
| 8,169,185 B2 | * | 5/2012 | Partovi et al. | 320/108 |
| 2004/0037442 A1 | | 2/2004 | Nielsen et al. | |
| 2005/0131491 A1 | | 6/2005 | Shaquer | |
| 2007/0104342 A1 | | 5/2007 | Seligman | |
| 2009/0216296 A1 | * | 8/2009 | Meskens | 607/57 |
| 2011/0130622 A1 | * | 6/2011 | Ilberg | 600/25 |
| 2013/0108091 A1 | * | 5/2013 | Stoffaneller et al. | 381/315 |

FOREIGN PATENT DOCUMENTS

| | | |
|---|---|---|
| JP | 2005-531175 A | 10/2005 |
| KR | 10-2011-0112856 A | 10/2011 |

OTHER PUBLICATIONS

International Search Report and Written Opinion for PCTIB2012/057087 Mailed Apr. 29, 2013.

* cited by examiner

*Primary Examiner* — Curtis Kuntz
*Assistant Examiner* — Ryan Robinson
(74) *Attorney, Agent, or Firm* — McDonnell Boehnen Hulbert & Berghoff LLP

(57) ABSTRACT

The present application discloses systems, methods, and articles of manufacture for determining prescription rules for a hearing prosthesis. A system in accordance with the present disclosure includes a receiver, a transmitter for wirelessly inducing electrical signals in the receiver, and first and second loads coupled to the receiver and associated with first and second applications, respectively. The system also includes a signal generator coupled to the transmitter. The signal generator is configured to energize the transmitter to transfer the electrical signals at a first duty cycle to the receiver for the first application and to energize the transmitter to transfer the electrical signals at a second duty cycle to the receiver for the second application.

37 Claims, 4 Drawing Sheets

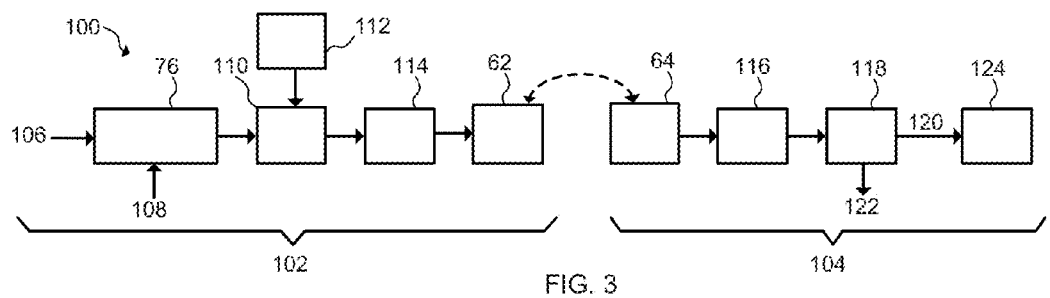
FIG. 3
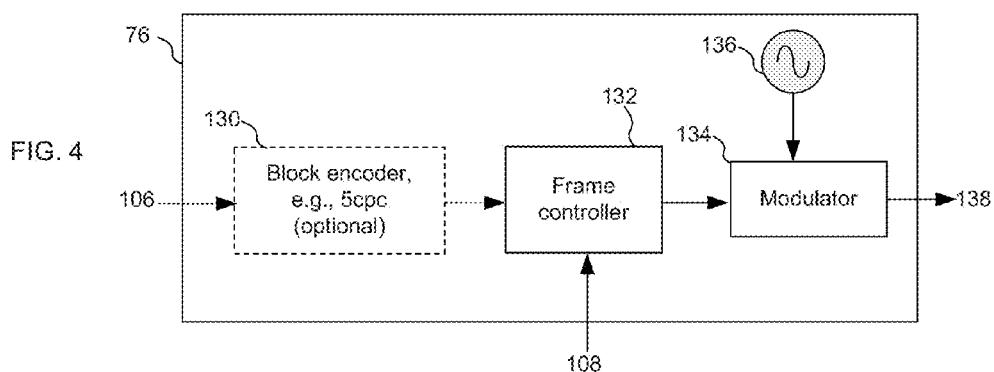
FIG. 4
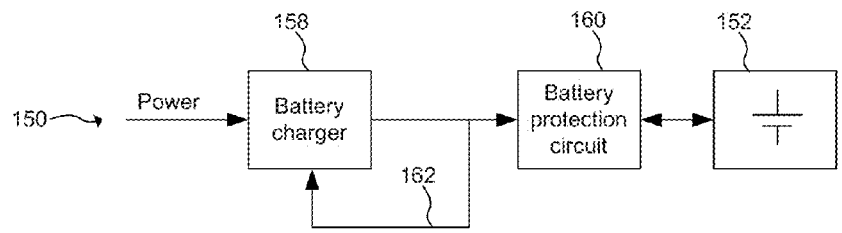
FIG. 5
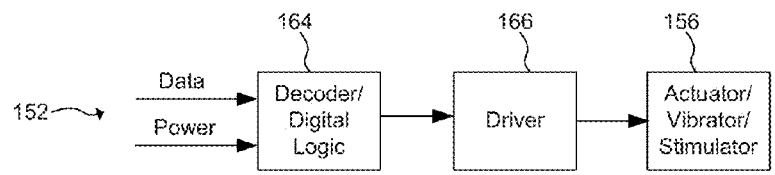

CONTROLLING A LINK FOR DIFFERENT LOAD CONDITIONS

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound and a vibration mechanism to apply vibrations corresponding to the detected sound directly or indirectly to a person's bone or teeth, thereby causing vibrations in the person's inner ear and bypassing the person's auditory canal and middle ear. Vibration-based hearing devices include, for example, bone anchored devices, direct acoustic cochlear stimulation devices, or other vibration-based devices. A bone-anchored device typically utilizes a surgically implanted mechanism or a passive connection through the skin or teeth to transmit vibrations corresponding to sound via the skull. A direct acoustic cochlear stimulation device also typically utilizes a surgically implanted mechanism to transmit vibrations corresponding to sound, but bypasses the skull and more directly stimulates the inner ear. Other non-surgical vibration-based hearing devices may use similar vibration mechanisms to transmit sound via direct or indirect vibration of teeth or other cranial or facial bones or structures.

Persons with certain forms of sensorineural hearing loss may benefit from prostheses, such as cochlear implants and/or auditory brainstem implants. For example, cochlear implants can provide a person having sensorineural hearing loss with the ability to perceive sound by stimulating the person's auditory nerve via an array of electrodes implanted in the person's cochlea. A component of the cochlear implant detects sound waves, which are converted into a series of electrical stimulation signals that are delivered to the implant recipient's cochlea via the array of electrodes. Auditory brainstem implants can use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound. Further, some persons may benefit from hearing prosthesis that combine one or more characteristics of the acoustic hearing aids, vibration-based hearing devices, cochlear implants, and auditory brainstem implants to enable the person to perceive sound.

Some hearing prostheses include separate units or elements that function together to enable the person to perceive sound. In one example, a hearing prosthesis includes a first element that is generally external to the person and a second element that can be implanted in the person. In the present example, the first element is configured to detect sound, to encode the detected sound as acoustic signals, to deliver the acoustic signals to the second element over a coupling or link between the first and second elements, and/or to deliver power to the second element over the link. The second element is configured to apply the delivered acoustic signals as output signals to the person's hearing system and/or to apply the delivered power to one or more components of the second element. The output signals applied to the person's hearing system can include, for example, audible signals, vibrations, and electrical signals, as described generally above.

The coupling or link between the first and second elements can be a radio frequency (RF) link operating in the magnetic or electric near-field, for example, and can be utilized to operate the hearing prosthesis in one or more modes, such as applying output signals to the person's hearing system and charging a power supply of the hearing prosthesis. In general, different operating modes of the hearing prosthesis may represent different load conditions that affect the efficiency of the coupling between the first and second elements. In various examples, the efficiency of the coupling can be optimized for a load condition of a particular operating mode or optimized for an average load condition of a plurality of operating modes, which results in a compromise design of the hearing prosthesis. In other examples, the first and second elements can include additional regulator and/or impedance matching circuitry to improve the efficiency of the coupling for different operating modes, which may come at the expense of adding size, complexity, and/or electrical losses to the hearing prosthesis. Generally, it is desirable to improve on the arrangements of the prior art or at least to provide one or more useful alternatives.

SUMMARY

The present application discloses systems, methods, and articles of manufacture for controlling a data and/or power coupling for different load conditions of a device or system. In one example, the coupling is configured to transfer power with or without data. Further, in various non-limiting examples, the system can be directed to a hearing prosthesis, such as a cochlear implant, a bone anchored device, a direct acoustic cochlear stimulation device, an auditory brain stem implant, an acoustic hearing aid, or any other type of hearing prosthesis configured to assist a recipient in perceiving sound.

Some embodiments of the present disclosure are directed to a system that includes a receiver, a transmitter for wirelessly transferring electrical signals to the receiver, and first and second loads coupled to the receiver and associated with first and second applications, respectively. The system also includes a signal generator coupled to the transmitter. The signal generator is configured to energize the transmitter to transfer the electrical signals at a first duty cycle to the receiver for the first application and to transfer the electrical signals at a second duty cycle to the receiver for the second application.

Other embodiments are directed to a method that includes inducing a first electrical signal over a wireless link at a first duty cycle in a receiver of a hearing prosthesis and supplying the first electrical signal to the hearing prosthesis to operate in a first mode. The method also includes inducing a second electrical signal over the wireless link at a second duty cycle in the receiver and supplying the second electrical signal to the hearing prosthesis to operate in a second mode.

Yet other embodiments are directed to a hearing prosthesis system that includes a primary coil, a secondary coil, and an output signal interface for applying acoustic signals to a user. The output signal interface can be coupled to the secondary coil. The system further includes a controller configured to energize the primary coil with first electrical signals for inducing second electrical signals in the secondary coil. The controller is configured to vary a duty cycle of the first electrical signals.

Other embodiments are directed to a method of improving the efficiency of an electromagnetic coupling of a hearing prosthesis for different loads that includes energizing a transmitter with first electrical signals to induce second electrical signals in a receiver of a hearing prosthesis and varying a duty cycle of the first electrical signals based on different loads coupled to the receiver.

Further embodiments are directed to a hearing prosthesis system that includes means for delivering electrical signals over a wireless link, means for receiving electrical signals over a wireless link, and means for applying output signals to a user. The means for applying is coupled to the means for receiving and an output signal applied to the user enables the user to perceive sound. The system also includes a controller configured to actuate the means for delivering with a first signal to deliver a second signal to the means for receiving. The controller is configured to vary a duty cycle of the first signal.

Still other embodiments are directed to an article of manufacture including instructions for energizing a first coil with first electrical signals to induce second electrical signals in a second coil of a hearing prosthesis and instructions for varying a duty cycle of the first electrical signals based on different load conditions coupled to the second coil.

BRIEF DESCRIPTION OF THE DRAWINGS

FIG. 3 illustrates a block diagram of first and second elements of a system according to an embodiment of the present disclosure;

FIG. 4 illustrates a block diagram of a signal generator of FIG. 3 in accordance with an embodiment of the present disclosure;

FIG. 5 illustrates a block diagram of a variable load corresponding to first and second operating modes of system, such as the system of FIG. 2, for example;

DETAILED DESCRIPTION

The following detailed description describes various features, functions, and attributes of the disclosed systems, methods, and articles of manufacture with reference to the accompanying figures. In the figures, similar symbols typically identify similar components, unless context dictates otherwise. The illustrative embodiments described herein are not meant to be limiting. Certain aspects of the disclosed systems, methods, and articles of manufacture can be arranged and combined in a variety of different configurations, all of which are contemplated herein.

For illustration purposes, some features and functions are described with respect to hearing prostheses. However, various features and functions disclosed herein may be applicable to other types of types of devices, including other types of medical and non-medical devices.

Figure 1:
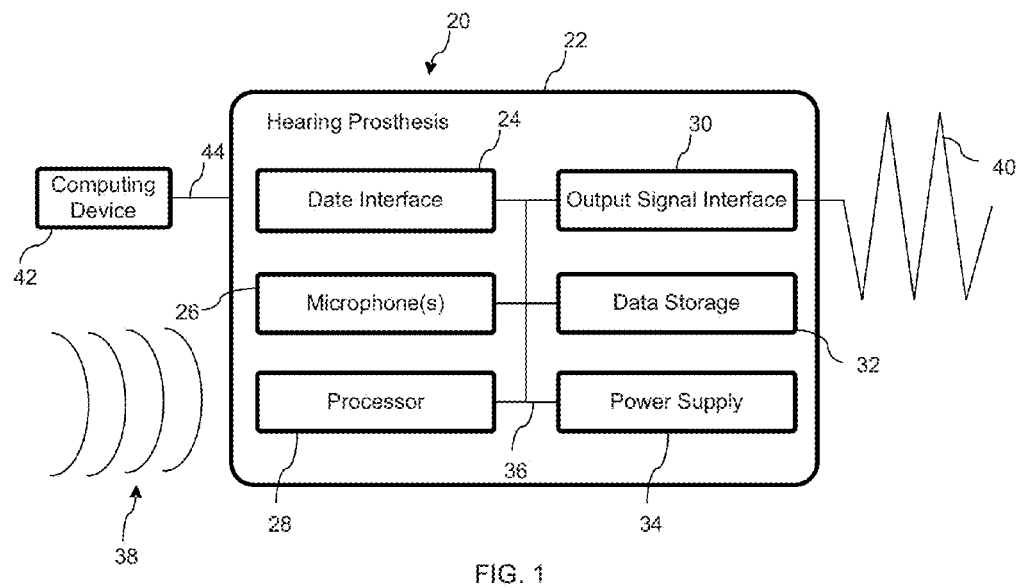
FIG. 1 illustrates a block diagram of a system according to an embodiment of the present disclosure.

Referring now to FIG. 1, an example system 20 includes a hearing prosthesis 22 configured according to some embodiments of the disclosed systems, methods, and articles of manufacture. In various examples, the hearing prosthesis 22 can be a cochlear implant, an acoustic hearing aid, a bone anchored device, a direct acoustic stimulation device, an auditory brain stem implant, or any other type of hearing prosthesis configured to assist a prosthesis recipient in perceiving sound.

The hearing prosthesis 22 illustrated in FIG. 1 includes a data interface 24, one or more microphones 26, one or more processors 28, an output signal interface 30, data storage 32, and a power supply 34 all of which are illustrated as being coupled directly or indirectly via a wired or wireless link 36. The one or more microphones 26 generally include combinations of one or more omnidirectional and directional microphones so that the hearing prosthesis 22 can be configured to process background sounds and/or to focus on sounds from a specific direction, such as generally in front of the prosthesis recipient.

Further, the power supply 34 supplies power to various components of the hearing prosthesis 22 and can be any suitable power supply, such as a non-rechargeable or rechargeable battery. In one example, the power supply 34 is a battery that can be recharged wirelessly, such as through inductive charging. Such a wirelessly rechargeable battery would facilitate complete subcutaneous implantation of the hearing prosthesis 22 to provide a fully implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis. A fully implanted hearing prosthesis also spares the recipient of stigma, imagined, or otherwise, associated with use of the prosthesis.

The data storage 32 generally includes any suitable volatile and/or non-volatile storage components. Further, the data storage 32 may include computer-readable program instructions and perhaps additional data. In some embodiments, the data storage 32 stores data and instructions used to perform at least part of the herein-described methods and algorithms and/or at least part of the functionality of the systems described herein.

Generally, in use, the microphone(s) 26 are configured to receive external acoustic signals 38 and the processor 28 is configured to analyze, amplify, and/or encode the acoustic signals into output signals 40. The output signals 40 can then be applied to the implant recipient via the output signal interface 30. The external acoustic signals 38 are generally encoded into the output signals 40 in accordance with configuration settings or data for a prosthesis recipient. The configuration settings can be stored in the data storage 32. A recipient's configuration settings allow the hearing prosthesis 22 to be configured for or fitted to a recipient. Generally, the configuration settings include gain prescription rules and other configuration data that defines how the processor 28 of the prosthesis 22 converts the acoustic signals 38 received by the microphone(s) 26 to output signals 40 transmitted to the prosthesis recipient via the output signal interface 30.

Illustratively, in embodiments where the hearing prosthesis 22 is a direct acoustic cochlear stimulation (DACS) device, the microphone(s) 26 are configured to receive acoustic signals 38 and the processor 28 is configured to analyze and encode the acoustic signals into mechanical vibration output signals 40. The mechanical vibration output signals 40 are applied to the DACS recipient's inner ear via the output signal interface 30 that, in the present example, includes an actuator to transmit sound via direct mechanical stimulation.

Similarly, for embodiments where the hearing prosthesis 22 is a bone anchored device, the microphone(s) 26 and the processor 28 are configured to receive, analyze, and encode acoustic signals 38 into mechanical vibration output signals 40. The mechanical vibration output signals 40 are applied to the bone anchored device recipient's skull via the output signal interface 30 that includes an actuator to transmit sound via direct bone vibrations, for example.

In addition, for embodiments where the hearing prosthesis 22 is an auditory brain stem implant, the microphone(s) 26 and the processor 28 are configured to receive, analyze, and encode the acoustic signals 38 into electrical stimulation output signals 40. The electrical stimulation output signals 40 are applied to the auditory brain stem implant recipient's auditory nerve via the output signal interface 30 that, in the present example, includes one or more electrodes.

Similarly, in embodiments where the hearing prosthesis 22 is a cochlear implant, the microphone(s) 26 and the processor 28 are configured to receive, analyze, and encode the external acoustic signals 38 into electrical stimulation output signals 40 that are applied to an implant recipient's cochlea via the output signal interface 30. In this example, the output signal interface includes an array of electrodes.

In embodiments where the hearing prosthesis 22 is an acoustic hearing aid or a combination electric and acoustic hybrid hearing prosthesis, the microphone(s) 26 and the processor 28 are configured to receive, analyze, and encode acoustic signals 38 into acoustic output signals 40 that are applied to a recipient's ear via the output signal interface 30 comprising a speaker, for example.

The system 20 illustrated in FIG. 1 further includes a computing device 42 that is configured to be coupled to the prosthesis 22 via a connection or link 44. The link 44 may be any suitable wired connection, such as an Ethernet cable, a Universal Serial Bus connection, a twisted pair wire, a coaxial cable, a fiber-optic link, or a similar physical connection, or any suitable wireless connection, such as Bluetooth, Wi-Fi, WiMAX, inductive or electromagnetic coupling or link, and the like.

In general, the computing device 42 and the link 44 can be used to operate the hearing prosthesis 22 in various modes. In a first example, the computing device 42 and the link 44 are used to develop and/or load a recipient's configuration data into the prosthesis 22, such as via the data interface 24. In another example, the computing device 42 and the link 44 are used to upload other program instructions and firmware upgrades, for example, to the hearing prosthesis 22. In yet other examples, the computing device 42 and the link 44 are used to deliver data and/or power to the hearing prosthesis 22 to operate the components thereof and/or to charge the power supply 34. Still further, various other modes of operation of the prosthesis 22 can be implemented by utilizing the computing device 42 and the link 44.

The computing device 42 can also include various components that are not shown explicitly in FIG. 1, such as a processor and a power source. Further, the computing device 42 can include use interface or input/output devices, such as buttons, dials, a touch screen with a graphic user interface, and the like, that can be used to turn the prosthesis 22 on and off, adjust the volume, switch between one or more operating modes, adjust or fine tune the configuration data, etc. Thus, the computing device 42 can be utilized by the recipient or a third party, such as a guardian of a minor recipient or a health care professional, to control the hearing prosthesis 22.

Various modifications can be made to the system 20 illustrated in FIG. 1. For example, user interface or input/output devices can be incorporated into the hearing prosthesis 22. Further, the hearing prosthesis 22 may include additional or fewer components arranged in any suitable manner. In some examples, the hearing prosthesis 22 may include other components to process external audio signals, such as components that measure vibrations in the skull caused by audio signals and/or components that measure electrical outputs of portions of a person's hearing system in response to audio signals.

Further, depending on the type and design of the hearing prosthesis 22, the illustrated components may be enclosed within a single operational unit or distributed across multiple operational units, for example, two or more internal units or an external unit and an internal unit. Generally, an internal unit can be hermetically sealed and adapted to be at least partially implanted in a person.

Illustratively, an external unit may include the computing device 42 and an internal unit may include the hearing prosthesis 22 of FIG. 1. In addition, the computing device 42 can include one or more of the components similar to the components 24-34 of the hearing prosthesis 22 of FIG. 1. For example, the computing device 42 can include one or more microphones for receiving the external acoustic signals 38 and a processor configured to analyze and encode the acoustic signals into output signals that are communicated to the data interface 24 of the hearing prosthesis 22 via the link 44. Typically, the computing device 42 also includes data storage for storing program instructions and other data. In addition, the computing device 42 generally includes a power supply to provide power to various components of the computing device and to provide power to the hearing prosthesis 22.

Figure 2:
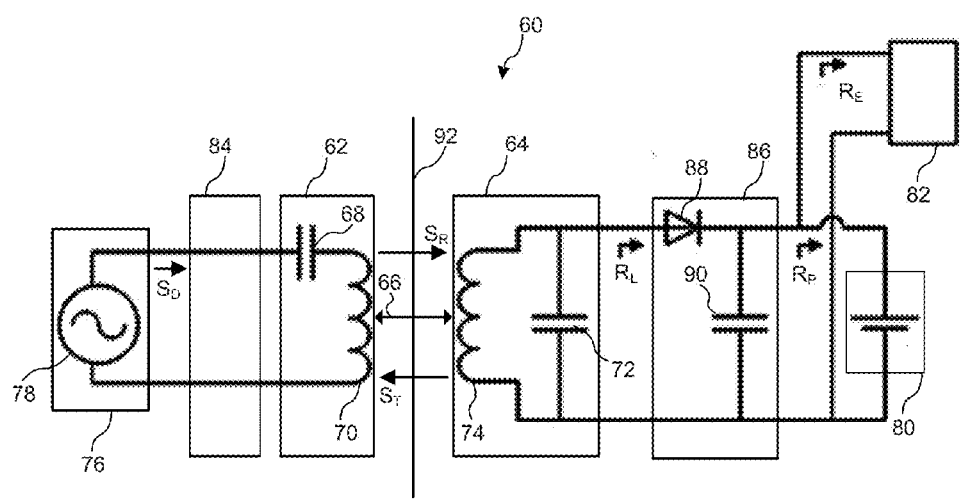
FIG. 2 illustrates a partial block, partial electrical schematic diagram of a system according to an embodiment of the present disclosure.

Referring now to FIG. 2, a partial block, partial electrical schematic diagram is illustrated of a system 60, which can be implemented as the system 20 and hearing prosthesis 22 in accordance with the example of FIG. 1. The system 60 shown in FIG. 2 includes a transmitter circuit 62 and a receiver circuit 64. In the present example, the transmitter circuit 62 and the receiver circuit 64 are associated with separate units or elements of the system 60, such as an external unit and an internal unit of a hearing prosthesis, respectively. The transmitter circuit 62 and the receiver circuit 64 are configured to deliver electrical signals therebetween via a link 66, such as an RF link operating in the magnetic or electric near-field. Generally, the circuits 62, 64 are configured to deliver electrical signals that include data and/or power over the link 66. In one example, the circuits 62, 64 are configured to deliver electrical signals that include power with or without data over the link 66.

As illustrated in FIG. 2, the transmitter circuit 62 can be modeled as a series LC tank circuit that includes a capacitor 68 and a primary coil 70 and the receiver circuit 64 can be modeled as a parallel LC tank circuit that includes a capacitor 72 and a secondary coil 74. In other examples, the transmitter and receiver circuits 62, 64 can include other arrangements and/or additional or fewer components.

The system 60 also includes a signal generator 76 coupled to the transmitter circuit 62. The signal generator 76 is configured to generate an electrical signal $S_D$ that is supplied to the transmitter circuit 62. More particularly, the electrical signal $S_D$ generated by the signal generator 76 and supplied to the transmitter circuit 62 induces or otherwise generates a corresponding electrical signal $S_R$ in the receiver circuit 64 to deliver power and/or data to the receiver circuit and other components coupled thereto. In one example, the electrical signal $S_D$ energizes the transmitter circuit 62 to generate a corresponding electrical signal $S_R$ in the receiver circuit 64 via an electromagnetic inductive link 66. In the present example, the signal generator 76 includes an oscillating power source 78 that generates an alternating current electrical signal $S_D$ that is supplied to the transmitter circuit 62. The alternating current of the signal $S_D$ generates a magnetic field from the primary coil 70 and the magnetic field induces the electrical signal $S_R$ in the secondary coil 74. The induced electrical signal $S_R$ can then be supplied to other components coupled to the receiver circuit 64.

As illustrated in FIG. 2, components coupled to the receiver circuit 64 include a power source 80 and system electronics 82. The system electronics 82 can include one or more hearing prosthesis electronics or components 24-32 discussed above in relation to FIG. 1. Further, FIG. 2 illustrates system electronics 84 coupled to the transmitter circuit 62. Similarly, the system electronics 84 can include one or more hearing prosthesis electronics or components 24-32 discussed above in relation to FIG. 1. Further, switching components can be coupled to the power source 80 and/or the system electronics 82 to allow the system 60 to switch between the various components in accordance with different operating modes.

Illustratively, the system electronics 84 coupled to the transmitter circuit 62 include a microphone 26 and a processor 28 for receiving acoustic signals 38 and encoding the acoustic signals into electrical signals $S_D$ that are supplied to the transmitter circuit by the signal generator 76. The signal generator 76 can also generate electrical signals $S_D$ supplied to the transmitter circuit 62 that are independent of the acoustic signals 38. As described above, the electrical signals $S_D$ supplied to the transmitter circuit 62 induce corresponding electrical signals $S_R$ in the receiver circuit 64. The induced electrical signals $S_R$ are supplied to other components coupled to the receiver circuit 64, such as the power source 80 and the system electronics 82, to operate the system 60 in one or more modes or applications. In one example, the induced electrical signals $S_R$ are supplied to the power source 80 to charge the power source. In another example, the induced electrical signals $S_R$ are supplied to a processor 28 and an output signal interface 30 of the system electronics 82 to encode the electrical signals as output signals 40 applied to a receipt or user of the system 60. In yet another example, the induced electrical signals $S_R$ are supplied to a data storage 32 of the system electronics 82 to load program instructions, software, firmware, data, etc. for use by the system 60.

Referring again to the system 60 of FIG. 2, a rectifier circuit 86 is coupled to the receiver circuit 64 to convert the electrical signals $S_R$ generated in the receiver circuit 64, which are typically alternating current signals, to direct current signals for use by one or more of the system electronics 82 and the power source 80. In the present example, the rectifier circuit 86 includes a diode 88 and a capacitor 90. Other rectifier circuits 86 can be used in other examples.

Referring now to FIG. 3, a block diagram of another system 100 similar to FIG. 2 is illustrated. The system 100 in the example of FIG. 3 includes a first element 102, such as an external unit of a hearing prosthesis, and a second element 104, such as an internal unit of a hearing prosthesis. Further, the system 100 includes a transmitter circuit 62, a receiver circuit 64, a link 66 between the circuits 62, 64, and a signal generator 76 similarly to FIG. 2.

In one example, the transmitter circuit 62 is a first antenna or coil structure and the receiver circuit 64 is a second antenna or coil structure. Further, in the present example, the signal generator 76 is an RF signal generator with frame or duty cycle control, as will be described in more detail hereinafter. Generally, the signal generator 76 of FIG. 3 receives a data input 106 and a frame control input 108 that can be utilized to generate a desired signal that is supplied to a driver 110. The driver 110 is configured to boost or amplify the signal from the signal generator 76 and may include, for example, a Class-D or Class-E amplifier with one or more MOSFET's or bipolar transistors. In addition, the system 100 of FIG. 3 includes a power supply 112 coupled to the driver 110 and/or other components of the first element 102. The first element 102 also includes an impedance matching component 114 coupled between the driver 110 and the transmitter circuit 62.

In the second element 104 of FIG. 3, an impedance matching component 116 is coupled to the receiver circuit 64 and a power and data extractor 118 is coupled to the impedance matching component. The power and data extractor 118 generates a power output 120 and a data output 122. FIG. 3 illustrates the power output 120 being supplied to a load 124. Alternatively or in combination, the data output 122 can also be supplied to the load 124. In various examples, the load 124 includes such components as the power source 80 and/or the system electronics 82 described above.

Referring now to FIG. 4, a block diagram of one example of the RF signal generator with frame control component 76 of FIG. 3 is illustrated. In FIG. 4, the signal generator 76 includes the data input 106 and the control input 108. The data input 106 is coupled to a block encoder 130, for example, a five cycle per cell encoder, for encoding data in the signal provided to the transmitter circuit 62 and transferred to the receiver circuit 64. The frame control input 108 is coupled to a frame or duty cycle controller 132, which is configured to vary a frame or duty cycle of the signal provided to the transmitter circuit 62, as will be described in more detail hereinafter. The frame controller 132 is also coupled to the block encoder 130 and to a modulator 134. As shown in the example of FIG. 4, an RF signal generator 136, which can generate a sinusoidal signal at 5 MHz, for example, is also coupled to the modulator 134. An output 138 from the modulator 134 is a frame or duty cycle controlled output signal that can be transferred from the transmitter circuit 62 to the receiver circuit 64.

Generally, the systems 60, 100 are configured to control or adjust the efficiency of the link 66 to deliver data and/or power between the transmitter circuit 62 and the receiver circuit 64. However, in some situations, the efficiency of the link 66 and, thus, the configuration and control of the systems 60, 100 are a function of a load condition of an operating mode of the system.

In one example, the power transfer efficiency of the link 66 in FIG. 2 can be approximated as a function of an effective load resistance $R_L$, looking into the rectifier circuit 86. Illustratively, if the electrical signal $S_D$ generated by the signal generator 76 is a constant sinusoidal signal, the effective load resistance $R_L$, looking into an ideal half-wave rectifier circuit can be approximated by the following Equation 1:

$$R_{L\_HW} = R/2 \quad (1)$$

In Equation 1, R is the resistance coupled to an output of the rectifier and can be measured in ohms or any other suitable unit. In the present example, the resistance R varies depending on an operating mode of the system 60. In FIG. 2, $R=R_P$ in a first operating mode when the power source 80 is being charged and $R=R_E$ in a second operating mode when supplying power and/or data to the system electronics 82, such as when the power source 80 is depleted. Further, the resistance $R_E$ can be one or more different resistance values depending on particular component(s) that are included in the system electronics 82 and/or on particular component(s) that are in use during an operating mode.

Illustratively, FIG. 5 shows examples of a first operating mode 150 during which a power source 152 is charged and a second operating mode 154 during which power and data are supplied to system electronics 156. In the first operating mode 150 of FIG. 3, power is supplied to the power source 152 through a battery charger component 158 and a battery protection circuit 160. Further, a feedback loop 162 can provide feedback data to the battery charger 158 for use in charging the power source 152. Such feedback data may include, for example, temperature, current, and voltage information related to the power supplied to the battery protection circuit 160.

In the second operating mode 154, signals including data and power are supplied to the system electronics 156 through a decoder/digital logic component 164 for decoding the data in the received signals and a driver 166 for amplifying the signals transferred to the system electronics 156. In FIG. 3, the system electronics 156 can include one or more of an actuator, vibrator, or other stimulator configured to apply output signals to a recipient.

Referring back to FIG. 2, varying load conditions for different operating modes of the system 60 complicate the process of configuring the system for optimal efficiency of the link 66. Prior systems have implemented a compromise design that results in sub-optimal performance or have included additional components for dynamically transforming the load conditions, at the expense of adding size, complexity, and/or electrical losses.

In contrast, the disclosed embodiments can be configured to optimize or at least improve the relative efficiency of the link 66 for different operating modes by controlling the electrical signals $S_D$ generated by the signal generator 76 and supplied to the transmitter circuit 62. More particularly, a duty cycle of the electrical signals $S_D$ generated by the signal generator 76 is varied for different operating modes and load conditions to optimize or at least improve the relative power transfer efficiency of the link 66. If the electrical signal $S_D$ generated by the signal generator 76 is provided to the transmitter circuit 62 in bursts, rather than continuously, the effective load resistance $R_L$ looking into an ideal half-wave rectifier 86 can be approximated by the following Equation 2:

$$R_{L\_HW} = D*(R/2) \quad (2)$$

In Equation 2, $R_{L\_HW}$ is the resistance coupled to an output of the rectifier 86 and D is the duty cycle of the electrical signal $S_D$. Generally, the duty cycle D is a fraction of time that the electrical signal $S_D$ is on or being generated by the signal generator 76 and supplied to the transmitter circuit 62. Using the relation in Equation 2, various components the system 60 can be configured to optimize the efficiency of the link 66 for a particular load condition or resistance and the duty cycle of the electrical signal $S_D$ generated by the signal generator 76 can be varied depending on the specific load condition. As a result, a single primary and second coil 72, 74 arrangement can be utilized to provide an efficient link 66 for different load conditions.

Illustratively, the system 60 can be operated in a first mode to charge the power source 80 and a second mode to deliver data and/or power to the system electronics 82. In the first mode, the power source 80 is a 4 V Li-ion battery that should be charged with a 20 mA charge current. In this case, the resistance looking into the power source 80 is $R_P=4V/0.02 A=200$ ohms. The load resistance $R_E$ looking into the system electronics 82, however, is typically significantly higher. For example, if the system electronics 82 requires 2 V and consumes only a 2 mA current, the resistance looking into the system electronics is $R_E=2V/0.002 A=1000$ ohms. For these parameters, an electrical signal $S_D$ can be generated with a duty cycle of 95% to charge the power source 80 and an electrical signal $S_D$ can be generated with a duty cycle of 19% to energize the system electronics 82. With these duty cycle values, the effective load resistance looking into the rectifier 86, as given by Equation 2, is the same in both cases to provide optimal power transfer efficiencies for the first and second modes.

Figure 6:
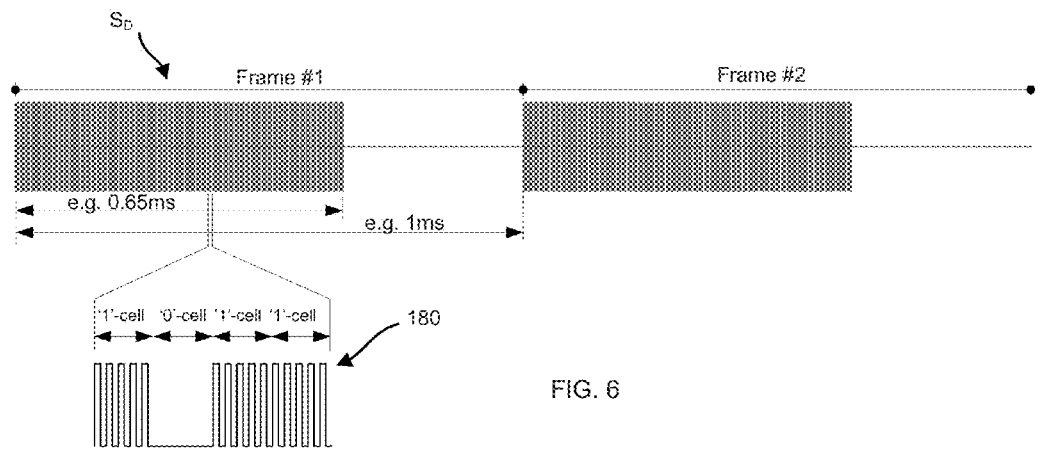
FIG. 6 illustrates an electrical signal having a 65% frame duty cycle in accordance with an embodiment of the present disclosure.

Referring to FIG. 6, a non-limiting example of the electrical signal $S_D$ at a duty cycle of about 65% is illustrated. In the example of FIG. 6, the duty cycle of a signal is generally considered to be a ratio of an On time to the total frame time or On and Off time. For example, in FIG. 6, the total frame time is 1 ms and the On time is 0.65 ms, which results in a 65% duty cycle. Further, FIG. 6 illustrates how data can be encoded in the electrical signal $S_D$, for example, using a five cycle per cell encoding. More particularly, within the On time of the signal $S_D$, binary one's and zero's can be encoded as shown in the enlarged portion 140. Further, the signal $S_D$ need not be a square wave, as generally illustrated. Rather, each signal burst can be modulated using known techniques, such as on-off keying (OOK), frequency-shift keying (FSK), phase-shift keying (PSK), and the like, to transfer power and/or data over the link 66.

In other examples, the system 60 can be operated in additional modes and the duty cycle of the electrical signal $S_D$ generated by the signal generator 76 can be adjusted accordingly. In one instance, the additional modes include different use cases that result in different load conditions. For example, the system 60 can be a hearing prosthesis and the different use cases may include an omnidirectional microphone mode, a directional microphone mode, a telephone mode, an audio/visual mode, etc. Another use case includes loading program instructions, such as firmware and software, over the link 66 and storing such program instructions in a data storage 32 of the system electronics 82.

The additional modes may also be associated with different duty cycles for different coupling factors between the transmitter circuit 62 and the receiver circuit 64. The different coupling factors can be the result of different distances between the transmitter and receiver circuits 62, 64 and different media 92 between the transmitter and receiver circuits. For example, different coupling factors can be the result of different skin flap characteristics and thicknesses that overlay an implanted receiver circuit 64. The coupling factor can be measured during a fitting or configuration process of the system 60 and/or can be monitored dynamically and accounted for while the system is in use.

Figure 7:
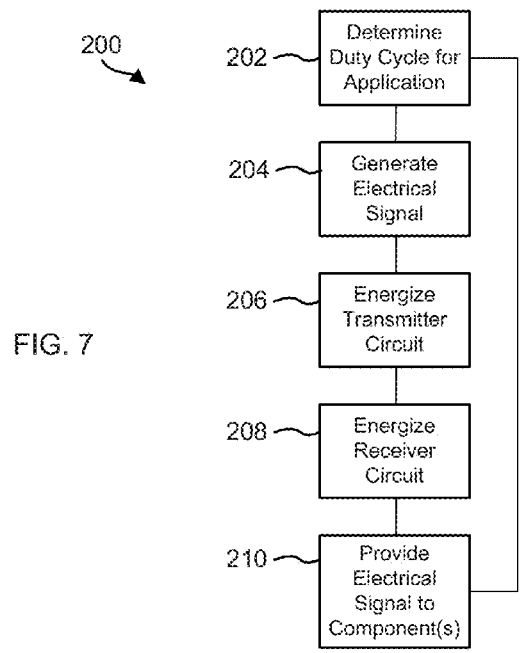
FIG. 7 is a flowchart showing a method or algorithm for using different duty cycles to optimize a link for different applications or operating modes according to an embodiment.

Still further, the signal generator 76 can dynamically adjust the duty cycle of the electrical signals $S_D$ to account for variations in the load conditions for different operating modes. The variations in the load conditions can be caused by a variety of factors, including the coupling factors and different operating modes described above. Further, variations in the load conditions can be caused by an amount of stimulation received by a hearing prosthesis, a level of signal processing, and other factors. The signal generator 76 can be configured to monitor current load conditions and vary the duty cycle of the electrical signal $S_D$ in real time to maintain improved efficiency of the link 66. In one example, the current load conditions can be derived from electrical signals $S_T$ that are fed back from the receiver circuit 64 to the transmitter circuit 62 through the link 66 and to the signal generator 76, which monitors the current load conditions and adjusts the duty cycle of the electrical signal $S_D$ accordingly. Referring now to FIG. 7 and with further reference the description above, one example method 200 is illustrated for using different duty cycles to optimize a link for different load conditions. For illustration purposes, some features and functions are described herein with respect to hearing prostheses. However, various features and functions may be equally applicable to other types of medical and non-medical devices.

The method 200 of FIG. 7 can be implemented by the systems 20, 60, 100 of FIGS. 1-3. Further, the method 200 may include one or more operations, functions, or actions as illustrated by one or more of blocks 202-210. Although the blocks 202-210 are illustrated in a sequential order, the blocks may also be performed in parallel, and/or in a different order than described herein. The method 200 may also include additional or fewer blocks, as needed or desired. For example, the various blocks 202-210 can be combined into fewer blocks, divided into additional blocks, and/or removed based upon a desired implementation.

In addition, each block 202-210 may represent a module, a segment, or a portion of program code, which includes one or more instructions executable by a processor for implementing specific logical functions or steps in the process. The program code may be stored on any type of computer readable medium or storage device including a disk or hard drive, for example. The computer readable medium may include non-transitory computer readable medium, such as computer-readable media that stores data for short periods of time like register memory, processor cache, and Random Access Memory (RAM). The computer readable medium may also include non-transitory media, such as secondary or persistent long term storage, like read only memory (ROM), optical or magnetic disks, compact-disc read only memory (CD-ROM), etc. The computer readable media may also include any other volatile or non-volatile storage systems. The computer readable medium may be considered a computer readable storage medium, for example, or a tangible storage device. In addition, one or more of the blocks 202-210 may represent circuitry that is wired to perform the specific logical functions of the method 200.

In the method 200, the block 202 determines a duty cycle for an application or operating mode of the system. More particularly, the block 202 determines the duty cycle for optimal efficiency of the application or operating mode. As discussed above, such duty cycle and optimal efficiency can vary based on the application and can be related to a number of factors, such as a load condition required by the application and a coupling factor of a data/power transfer link. Further, the duty cycle can be dynamically varied based on changing load conditions that can be continuously monitored, as described generally above.

The block 204 generates an electrical signal with the duty cycle determined by the block 202. In one example, the block 204 controls the signal generator 76 to generate the electrical signal $S_D$ with the determined duty cycle. In the present example, other parameters of the electrical signal $S_D$ are also determined based on the given application, such as an amplitude, frequency, period, etc. to encode data and/or deliver power, as needed for the application.

In FIG. 7, the block 206 supplies the electrical signal, such as the signal $S_D$, to energize a transmitter circuit, such as the transmitter circuit 62 of FIG. 2. The block 208 energizes a receiver circuit, such as the receiver circuit 64 of FIG. 2, in response to the block 206. In one example, the electrical signal $S_D$ energizes the transmitter circuit 62 to induce a corresponding electrical signal $S_R$ in the receiver circuit 64 via the link 66. Thereafter, the block 210 provides the electrical signal to one or more components in accordance with the given application, for example, the electrical signal $S_R$ can be provided to hearing prosthesis electronics to provide power and data thereto or to charge a power source.

In the method 200 of FIG. 7, after the block 210, control passes back to the block 202 to determine whether the duty cycle is the same or has changed and the processing of blocks 202-210 can be performed thereafter, as described above.

Figure 8:
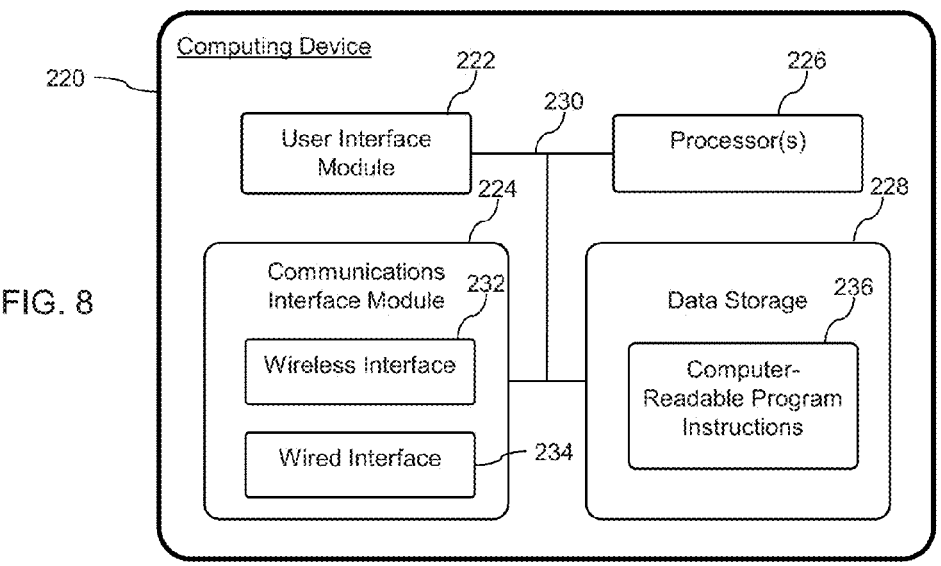
FIG. 8 illustrates a block diagram of a computing device according to an embodiment that can be used to implement certain aspects of the disclosed systems, methods, and articles of manufacture.

Referring now to FIG. 8, a computing device 220 is illustrated, which may be the same or different from the computing device 42 of FIG. 1. Generally, the computing devices 42, 220 can be used to implement aspects of various embodiments of the disclosed systems, methods, and articles of manufacture. For example, the computing devices 42, 220 can include or be coupled to components of the transmitter circuit 62, the signal generator 76, and the system electronics 84 of FIG. 2.

In FIG. 8, the computing device 220 includes a user interface module 222, a communications interface module 224, one or more processors 226, and data storage 228, all of which are linked together via a system bus or other connection mechanism 230. The user interface module 222 is configured to send data to and/or receive data from user input/output devices such as a keyboard, a keypad, a touch screen, a computer mouse, a track ball, a joystick, and/or other similar devices, now known or later developed. Additionally, the user interface module 222 is also configurable to provide outputs to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 222 may also be configured to generate audible output(s), such as a speaker, speaker jack, audio output port, audio output device, earphones, and/or other similar devices, now known or later developed.

The communications interface module 224 includes one or more wireless interfaces 232 and/or wired interfaces 234 configured to send and receive data to and/or from other devices and systems, such as a hearing prosthesis, via a communications link, such as the connection 44 of FIG. 1. The wireless interfaces 232 may include one or more wireless transceivers, such as a Bluetooth transceiver, a Wi-Fi transceiver, a WiMAX transceiver, electromagnetic inductive link transceiver, and/or other similar types of wireless transceiver configurable to communicate via a wireless protocol. The wired interfaces 234 may include one or more wired transceivers, such as an Ethernet transceiver, a Universal Serial Bus (USB) transceiver, or similar transceiver configurable to communicate via a twisted pair wire, a coaxial cable, a fiber-optic link, or a similar physical connection.

The one or more processors 226 may include one or more general purpose processors, such as microprocessors manufactured by Intel, Apple, Advanced Micro Devices, etc., and/or one or more special purpose processors, such as digital signal processors, application specific integrated circuits, etc.

The one or more processors 226 are configured to execute computer readable program instructions 236 stored in the data storage 228, such as instructions to perform aspects of the method 200 of FIG. 7.

The data storage 228 includes one or more computer readable storage media that can be read or accessed by at least one of the processors 226. The one or more computer-readable storage media includes volatile and/or non-volatile storage components, such as optical, magnetic, organic, or other memory or disc storage, which can be integrated in whole or in part with at least one of the processors 226. In some embodiments, the data storage 228 is implemented using a single physical device, such as one optical, magnetic, organic or other memory, or disc storage unit, while in other embodiments, the data storage is implemented using two or more physical devices. In the present example, the data storage 228 includes the computer readable program instructions 236 and perhaps additional data. In some embodiments, the data storage 228 includes storage required to perform at least some aspects of the method of FIG. 7.

In some embodiments, the disclosed features and functions of the systems and methods shown and described herein may be implemented as computer program instructions encoded on computer-readable media in a machine-readable format.

Figure 9:
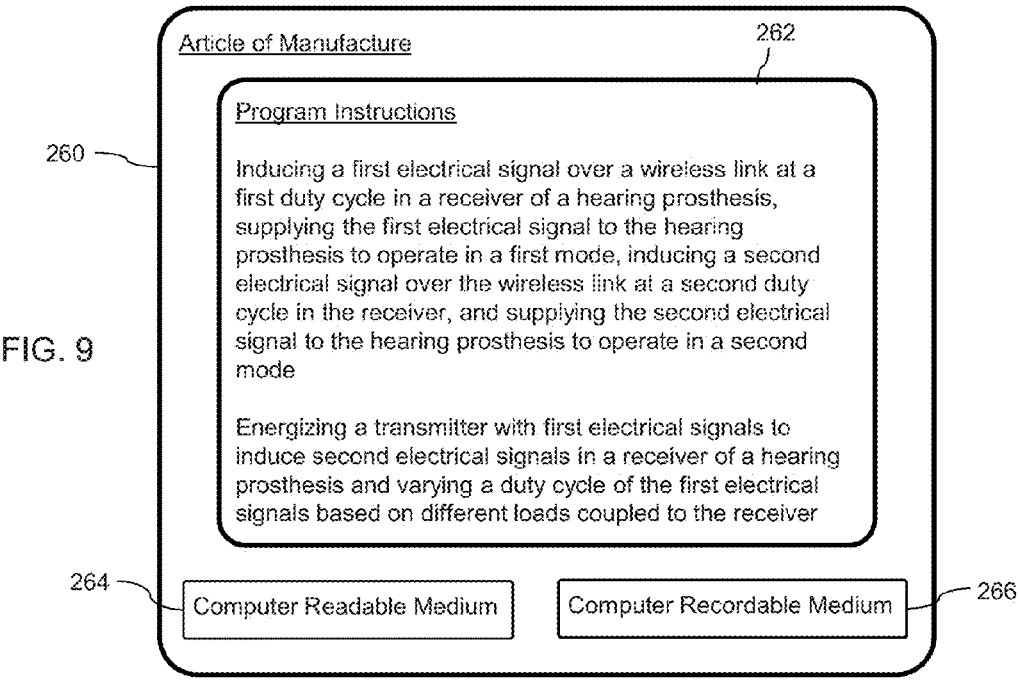
FIG. 9 is a block diagram of an article of manufacture including computer-readable media with instructions for using different duty cycles to optimize a link according to an embodiment.

FIG. 9 shows an example of an article of manufacture 260 including computer readable media with instructions 262 for using different duty cycles to optimize a link. In FIG. 9, the example article of manufacture 260 includes computer program instructions 262 for executing a computer process on a computing device, arranged according to at least some embodiments described herein.

In some examples, the article of manufacture 260 includes a computer-readable medium 264, such as, but not limited to, a hard disk drive, a Compact Disc (CD), a Digital Video Disk (DVD), a digital tape, flash memory, etc. In some implementations, the article of manufacture 260 includes a computer recordable medium 266, such as, but not limited to, a hard disk drive, a Compact Disc (CD), a Digital Video Disk (DVD), a digital tape, flash memory, etc.

The one or more programming instructions 262 include, for example, computer executable and/or logic implemented instructions. In some embodiments, a computing device such as the processor 28, the computing device 42, and/or the computing device 220, alone or in combination with one or more additional processors or computing devices, may be configured to perform certain operations, functions, or actions to implement the features and functionality of the disclosed systems and methods based at least in part on the programming instructions 262.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system comprising:
    a receiver;
    a transmitter for wirelessly transferring electrical signals to the receiver;
    first and second loads coupled to the receiver and associated with first and second applications, respectively;
    a signal generator coupled to the transmitter, wherein the signal generator is configured to energize the transmitter to transfer the electrical signals at a first duty cycle to the receiver for the first application, wherein the signal generator is configured to energize the transmitter to transfer the electrical signals at a second duty cycle to the receiver for the second application, and wherein the first duty cycle is defined by a ratio between an On time and a frame time for the first application and the second duty cycle is defined by a ratio between the On time and the frame time for the second application.

2. The system of claim 1, wherein the first load is a power source and the second load includes hearing prosthesis electronics.

3. The system of claim 2, wherein the first duty cycle is greater than the second duty cycle.

4. The system of claim 2, wherein the first application charges the power source and the second application delivers data to the hearing prosthesis electronics.

5. The system of claim 4, wherein the data includes acoustic signal data.

6. The system of claim 4, wherein the second application delivers power and data to the hearing prosthesis electronics.

7. The system of claim 4, wherein the data is block encoded within the On time of the frame time for the second application.

8. The system of claim 1, further comprising a third load coupled to the receiver and associated with a third application, wherein the signal generator is configured to energize the transmitter to induce the electrical signals at a third duty cycle in the receiver for the third application, wherein the third duty cycle is defined by a ratio between an On time and a frame time for the third application.

9. The system of claim 8, wherein the third load includes a data storage, and wherein the third application delivers program instructions to the data storage.

10. The system of claim 1, wherein the transmitter includes a primary coil circuit and the receiver includes a secondary coil circuit.

11. The system of claim 1, wherein the transmitter is configured to wirelessly transfer electrical signals to the receiver via a coupled antenna structure.

12. The system of claim 1, wherein the transmitter is configured to wirelessly transfer electrical signals to the receiver over magnetically coupled coils in a near-field.

13. The system of claim 1, wherein the receiver and the first and second loads are enclosed within a single operational unit.

14. The system of claim 13, wherein the single operational unit is hermetically sealed and adapted to be at least partially implanted in a person.

15. A method comprising:
    inducing, in a receiver of a hearing prosthesis for operation in a first mode, a first electrical signal over a wireless link, wherein the first electrical signal has a first duty cycle, and wherein the first mode corresponds to the wireless link having a first coupling factor; and
    inducing, in the receiver for operation in a second mode, a second electrical signal over the wireless link, wherein the second electrical signal has a second duty cycle, and wherein the second mode corresponds to the wireless link having a second coupling factor,
    wherein the first duty cycle is defined by a ratio between an On time and a frame time for the first mode and the second duty cycle is defined by a ratio between the On time and the frame time for the second mode.

16. The method of claim 15, further comprising supplying the first electrical signal to a power source of the hearing prosthesis, and supplying the second electrical signal to hearing prosthesis electronics of the hearing prosthesis.

17. The method of claim 16, wherein the first mode includes charging the power source and the second mode includes delivering data to the hearing prosthesis electronics.

18. The method of claim 17, wherein the second mode includes delivering power and data to the hearing prosthesis electronics.

19. The method of claim 15, wherein at least one of the first and second modes includes receiving program instructions for the hearing prosthesis.

20. The method of claim 15, wherein the hearing prosthesis is configured to be at least partially subcutaneously implanted, and wherein the first coupling factor corresponds to a first skin thickness over the receiver and the second coupling factor corresponds to a second skin thickness over the receiver.

21. A hearing prosthesis system comprising:
a primary coil;
a secondary coil;
an output signal interface for applying output signals to a user, the output signal interface being coupled to the secondary coil; and
a controller configured to energize the primary coil with first electrical signals for inducing second electrical signals in the secondary coil, wherein the first electrical signals have a duty cycle, and wherein the controller is configured to dynamically vary the duty cycle of the first electrical signals in response to varying loads coupled to the secondary coil,
wherein the duty cycle is defined by a ratio between an On time and a frame time of the first electrical signals.

22. The system of claim 21, wherein the controller is configured to vary the duty cycle of the first electrical signals to a first level for inducing the second electrical signals to charge a power source coupled to the secondary coil and to vary the duty cycle of the first electrical signals to a second level for inducing the second electrical signals to cause the output signal interface to apply output signals to the user.

23. The system of claim 22, wherein the controller is configured to vary the duty cycle of the first electrical signals to a third level for inducing the second electrical signals to load computing instructions to a storage device coupled to the secondary coil.

24. The system of claim 21, wherein the controller is configured to vary the duty cycle of the first electrical signals to a first level for inducing the second electrical signals over a first wireless link and to a second level for inducing the second electrical signals over a second wireless link.

25. The system of claim 24, wherein the secondary coil is configured to be subcutaneously implanted, and wherein the first wireless link corresponds to a first coupling factor and the second wireless link corresponds to a second coupling factor.

26. The system of claim 21, wherein the secondary coil is configured to induce third electrical signals in the primary coil indicative of the varying loads, and wherein the controller is configured to process the third electrical signals to vary the duty cycle of the first electrical signals.

27. A method comprising:
energizing a transmitter with first electrical signals to induce second electrical signals in a receiver of a hearing prosthesis, wherein the first electrical signals have a duty cycle; and
varying the duty cycle of the first electrical signals based on different loads coupled to the receiver, wherein the step of varying the duty cycle includes setting the duty cycle to a first level for inducing the second electrical signals to charge a power source coupled to the receiver, and setting the duty cycle to a second level for inducing the second electrical signals to apply output signals to a user of the hearing prosthesis,
wherein the duty cycle is defined by a ratio between an On time and a frame time of the first electrical signals.

28. The method of claim 27, wherein the step of varying a duty cycle includes setting the duty cycle of the first electrical signals to a third level for inducing the second electrical signals to load computing instructions to a storage device coupled to the receiver.

29. The method of claim 27, wherein the step of varying a duty cycle includes setting the duty cycle of the first electrical signals to a third level for inducing the second electrical signals over a first wireless link and to a fourth level for inducing the second electrical signals over a second wireless link.

30. The method of claim 29, wherein the receiver is configured to be subcutaneously implanted, and wherein the first wireless link corresponds to a first coupling factor and the second wireless link corresponds to a second coupling factor.

31. The method of claim 27, further comprising inducing third electrical signals in the transmitter indicative of the different loads and processing the third electrical signals to vary the duty cycle of the first electrical signals.

32. A hearing prosthesis system comprising:
means for delivering electrical signals over a wireless link;
means for receiving electrical signals over a wireless link;
means for applying output signals to a user, wherein the means for applying is coupled to the means for receiving, and wherein an output signal applied to the user enables the user to perceive sound; and
a controller configured to actuate the means for delivering with a first signal to deliver a second signal to the means for receiving, wherein the first signal has a duty cycle, and wherein the controller is configured to vary the duty cycle of the first signal to a first level to deliver the second signal over a first wireless link, and to vary the duty cycle of the first signal to a second level to deliver the second signal over a second wireless link,
wherein the duty cycle is defined by a ratio between an On time and a frame time of the first signal.

33. The system of claim 32, wherein the controller is configured to vary the duty cycle of the first signal to a third level to deliver the second signal to charge a power source coupled to the means for receiving and to vary the duty cycle of the first signal to a fourth level to deliver the second signal to cause the means for applying to apply the output signal to the user.

34. The system of claim 33, wherein the controller is configured to vary the duty cycle of the first signal to a fifth level to deliver the second signal to load computing instructions to a storage device coupled to the means for receiving.

35. The system of claim 32, wherein the means for receiving is configured to be subcutaneously implanted, and wherein the first wireless link corresponds to a first coupling factor and the second wireless link corresponds to a second coupling factor.

36. The system of claim 32, wherein the controller is configured to dynamically vary the duty cycle of the first signal in response to different loads coupled to the means for receiving.

37. The system of claim 36, wherein the means for receiving is configured deliver a third signal to the means for delivering, wherein the third signal is related to the different loads, and wherein the controller is configured to process the third signal to vary the duty cycle of the first signal.

* * * * *